United States Patent

Neame et al.

[11] Patent Number: 5,979,445
[45] Date of Patent: Nov. 9, 1999

[54] LARYNGEAL MASK AIRWAYS AND THEIR MANUFACTURE

[75] Inventors: Simon Neame, Broadstairs; Eric Pagan, Hythe, both of United Kingdom

[73] Assignee: Smiths Industries Public Limited Company, London, United Kingdom

[21] Appl. No.: 08/956,358

[22] Filed: Oct. 23, 1997

[30] Foreign Application Priority Data

Nov. 2, 1996 [GB] United Kingdom ................... 9622880

[51] Int. Cl.$^6$ .................................................. A61M 16/00
[52] U.S. Cl. ............................... 128/207.15; 128/207.14; 128/200.26
[58] Field of Search .................... 128/207.15, 207.14, 128/200.26, 206.26; 604/96, 103, 174

[56] References Cited

U.S. PATENT DOCUMENTS

| | | |
|---|---|---|
| 4,509,514 | 4/1985 | Brain . |
| 4,995,388 | 2/1991 | Brain .................................. 128/207.15 |
| 5,297,547 | 3/1994 | Brain .................................. 128/207.15 |
| 5,305,743 | 4/1994 | Brain .................................. 128/207.15 |
| 5,391,248 | 2/1995 | Brain .................................. 128/207.15 |
| 5,443,063 | 8/1995 | Greenberg . |
| 5,682,880 | 11/1997 | Brain .................................. 128/207.14 |
| 5,694,929 | 12/1997 | Christopher ....................... 128/207.14 |
| 5,771,889 | 6/1998 | Pagan ................................. 128/200.26 |

FOREIGN PATENT DOCUMENTS

| | | |
|---|---|---|
| 0 448 878 | 10/1991 | European Pat. Off. ....... A61M 16/04 |
| 0712638A1 | 5/1996 | European Pat. Off. . |

*Primary Examiner*—John G. Weiss
*Assistant Examiner*—V. Srivastava
*Attorney, Agent, or Firm*—Pollock, Vande Sande & Amernick

[57] ABSTRACT

A laryngeal mask assembly has a mask portion of elliptical shape formed by a mount and an inflatable member attached to the mount. The inflatable member is formed by heat bonding together opposite walls of a flat balloon and at the same time cutting an aperture through the walls, so as to form a central web within an outer inflatable ring. The central web is attached to a concave surface on the forward surface of the mount with the aperture in the web aligned with an opening in the mount.

6 Claims, 2 Drawing Sheets

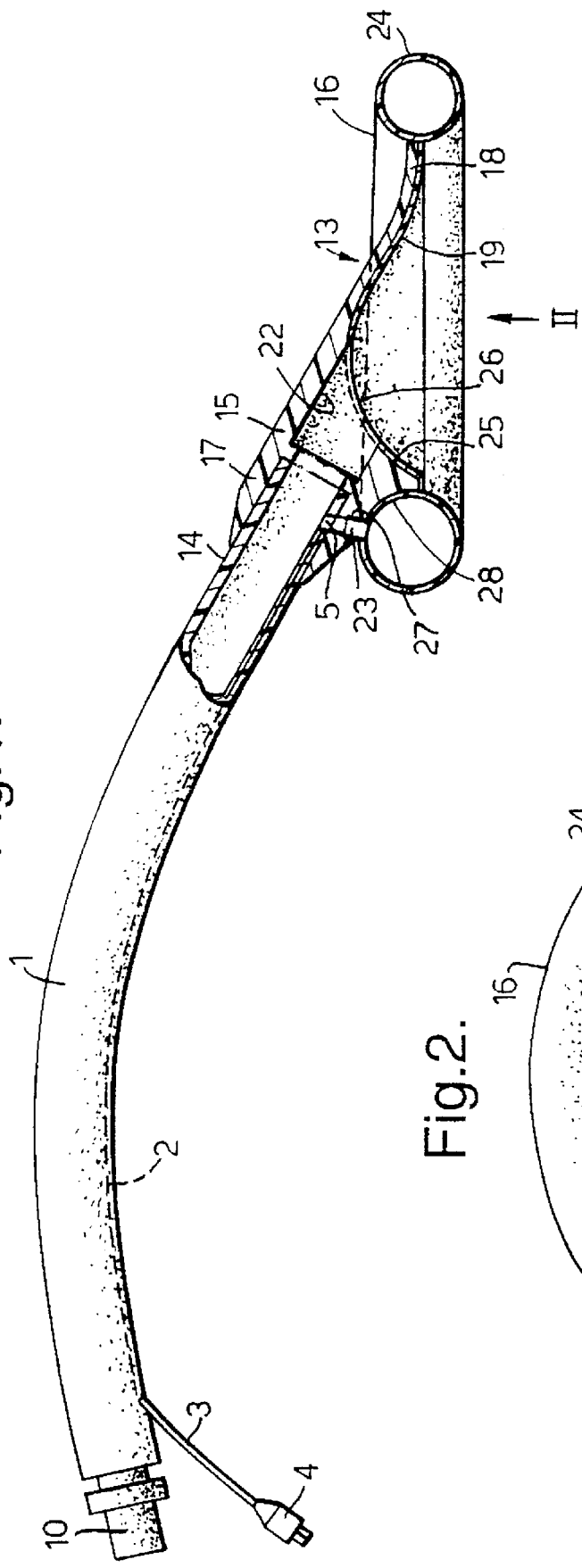
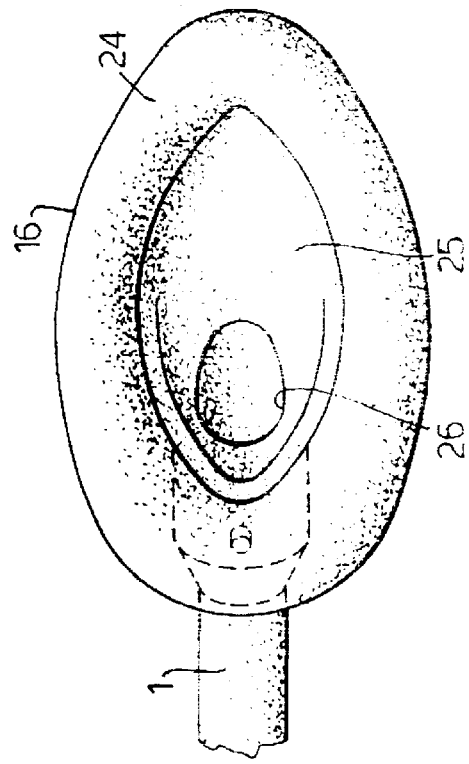

LARYNGEAL MASK AIRWAYS AND THEIR MANUFACTURE

CROSS REFERENCE TO RELATED APPLICATIONS

The subject matter of the present invention is related to the inventions described in Neame et al., U.S. application Ser. No. 08/925,668, filed Sep. 9, 1997 for "Laryngeal Mask Airways and their Manufacture", now U.S. Pat. No. 5,871,012 and Neame, U.S. application Ser. No. 08/961,038, filed Oct. 30, 1997 for "Laryngeal Mask Airways and their Manufacture" now U.S. Pat. No. 5,881,726.

BACKGROUND OF THE INVENTION

This invention relates to laryngeal mask airways and their manufacture.

It is common practice to use an airway known as a laryngeal mask for the administration of anaesthetic and ventilation gases to a patient. These airways comprise a tube with an inflatable mask or cuff at one end, the tube being inserted in the patient's mouth so that one end is located in the hypopharynx and so that the mask forms a seal in this region with the surrounding tissue. Laryngeal masks are described in, for example, U.S. Pat. No. 5,355,879, U.S. Pat. No. 5,305,743, U.S. Pat. No. 5,297,547, U.S. Pat. No. 5,282,464, GB 2267034, U.S. Pat. No. 5,249,571, U.S. Pat. No. 5,241,956, U.S. Pat. No. 5,303,697, GB 2249959, GB 2111394, EP 448878, U.S. Pat. No. 4,995,388, GB 2205499, GB 2128561 and GB2298797.

Laryngeal masks have several advantages over endotracheal tubes, which are longer and seal with the trachea below the vocal folds. It can be difficult, however, to manufacture the patient end of the mask at low cost.

BRIEF SUMMARY OF THE INVENTION

It is an object of the present invention to provide an improved laryngeal mask assembly and method of manufacture.

According to one aspect of the present invention there is provided a laryngeal mask assembly including a mask portion and an elongate tube that opens at its forward, patient end into the mask portion, the mask portion being adapted during use to locate in the hypopharynx and to open on its forward side to the patient's airway, the mask portion having a mount member attached with the patient end of the tube, the mount member being generally elliptical, the tube opening at the patient end of the assembly via an opening on the forward surface of the mount member, and the mask portion having an inflatable member comprising an inflatable ring and a central web extending within said ring, the web being attached to the forward surface of the mount member and having an aperture therein aligned with the opening in said mount member.

According to another aspect of the present invention there is provided a method of manufacture of a laryngeal mask assembly of the kind including a mask portion and an elongate tube that opens at its forward, patient end into the mask portion, the mask portion being adapted during use to locate in the hypopharynx and to open on its forward side to the patient's airway, the method including the steps of providing a mount member at the patient end of the tube, forming an inflatable member comprising an inflatable ring and a web within the ring, and attaching the web to the mount member so as to secure the inflatable member with the mount member.

The inflatable member may be made by providing a generally elliptical balloon and securing opposite walls of the balloon together in a central region so that the central region provides said web and the region around the central region provides said inflatable ring.

A laryngeal mask assembly and its method of manufacture, according to the present invention, will now be described, by way of example, with reference to the accompanying drawings.

BRIEF DESCRIPTION OF THE DRAWINGS

FIG. 1 is a partly-sectional side elevation view of the assembly;

FIG. 2 is a view of the forward end of the assembly along the arrow II of FIG. 1;

DETAILED DESCRIPTION OF THE PREFERRED EMBODIMENT

Figure 3:
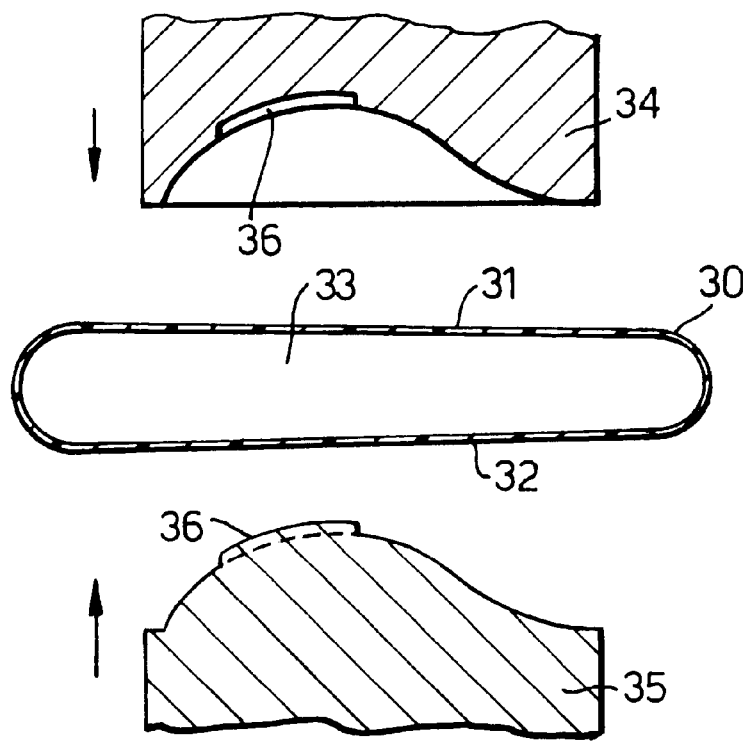
FIGS. 3 and 4 illustrate steps in the manufacture of the inflatable member.

With reference to FIGS. 1 and 2, the assembly comprises a bendable tube 1 of a plastics material, such as PVC, with a coupling 10 at its machine end 12. The tube 1 is curved along its length and has a mask portion 13 at its patient end 14.

The tube 1 is extruded with an inflation lumen 2 within its wall. The lumen 2 is connected towards the machine end of the assembly to an inflation line 3 with an inflation indicator and connector 4. The opposite, patient end of the inflation lumen 2 opens into the mask portion 13, through a hole or slot 5 formed in the outside of the tube 1.

The mask portion 13 comprises a mount member 15 and an expandable or inflatable assembly 16. The mount member 15 is moulded from a relatively stiff plastics material, such as PVC. The mount member 15 has a hollow cylindrical sleeve 17 at its rear end, in which the forward, patient end of the tube 1 is inserted and joined. The forward, patient end 18 of the mount member 15 is of an inverted dish shape with a generally elliptical or egg-shape outline and with a concave surface or recess 19. A bore 22 extends forwardly through the mount member 15, as a continuation of the bore through the sleeve 17, and forms an opening into the rear part of the recess 19. The hole or slot 5 in the tube 1 opens into a passage 23 through the mount member 15.

The inflatable assembly 16 comprises an expandable or inflatable outer ring 24 of circular section and egg shape with an integral, flexible, central web 25 within the ring. The ring 24 could have other shape sections, such as oval or elliptical. The diameter of the ring 24 towards the rear, machine end is slightly greater than that at the forward, patient end. The web 25 has the same shape as the underside of the mount member 15, that is, it is concave when viewed from beneath. An aperture 26 through the web 25 is aligned with the opening of the bore 22 in the mount member 15. A spigot 27 projects upwardly from the ring 24 and is sealed within the passage 23 in the mount member 15 so that the inflation lumen 2 opens into the ring 24. The inflatable member 16 is attached to the mount member 15 by means of an adhesive between the upper surface of the web 25 and the surface of the recess 19 so that the ring 24 projects beyond the mount member around its perimeter. Adhesive is also applied in the region of the passage 23, where the mount member has a shallow concave recess 28 shaped to receive a part of the ring 24 around the spigot 27.

Figure 4:
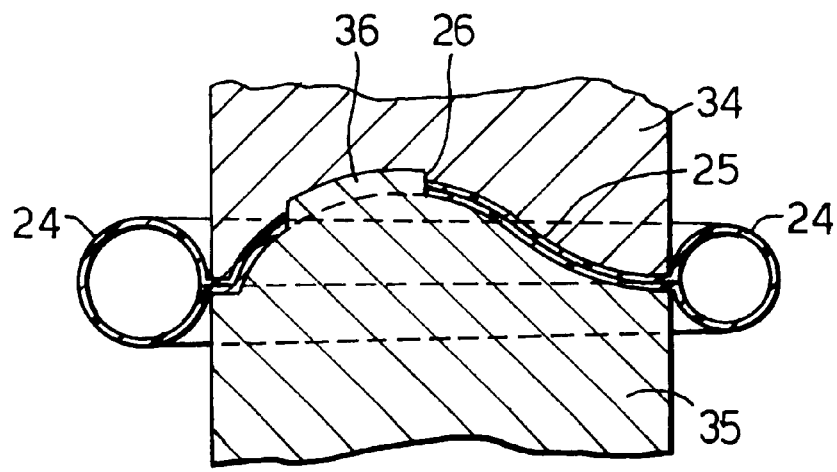

The inflatable member 16 can be readily manufactured from a flexible plastics material, such as PVC, polyurethane, silicone, EVA, TPE, polyether block amide or the like. In one method of manufacture, a flat balloon 30 is first blow moulded having the egg-shape outline of the assembly but with substantially flat upper and lower surfaces 31 and 32 and an open interior 33, as shown in FIG. 3. The balloon 30 is then placed between two dies 34 and 35, which are brought together to force the upper and lower surfaces 31 and 32 into contact in the central region only, leaving the surfaces separate in the peripheral region, as shown in FIG. 4. The dies 34 and 35 are heated so that the upper and lower surface heat bond together in the central region to form the web 25, the peripheral region outside the central region forming the inflatable ring. Alternatively, the bond could be made by RF welding. The die surfaces have complementary profiles, defining the finished shape of the web, and cutting edges 36 to form the aperture 26 in the web. The spigot 27 may be formed during the initial blow moulding process or attached subsequently. The aperture 26 could have a series of holes or slits to prevent entry of the epiglottis.

The airway can be easily manufactured in this way at low cost.

The expandable member 16 could contain a foam material so that it naturally adopts an inflated or expanded state and is deflated by the action of suction. The foam may be inserted in the ring after attaching the expandable member to the mount member.

What we claim is:

1. A laryngeal mask assembly comprising: a mask portion that is adapted during use to locate in the hypopharynx of a patient and to open on a forward side of the mask portion to the patient's airway; and an elongate tube that opens at a forward patient end of said tube into said mask portion, said mask portion having a mount member attached with said patient end of said tube, said mount member being generally elliptical and having an opening on a forward surface of said mount member, said tube opening at a patient end of said assembly via said opening in said mount member, said mask portion having a one-piece inflatable member comprising an inflatable ring and a central web extending within said ring, said central web comprising two flexible walls integral with said ring and bonded together, and said web being attached to said forward surface of said mount member and having an aperture therein aligned with said opening in said mount member.

2. A laryngeal mask assembly according to claim 1, wherein said forward surface of said mount member is concave.

3. A laryngeal mask assembly according to claim 1, wherein said ring projects beyond an outer perimeter of said mount member.

4. A method of manufacture of a laryngeal mask assembly of the kind including a mask portion and an elongate tube that opens at a forward, patient end of said tube into said mask portion, said mask portion being adapted during use to locate in the hypopharynx of a patient and to open to the patient's airway on a forward side of said mask portion, the method including the steps of providing a mount member at a patient end of said tube, forming an expandable balloon having two opposite walls, joining said opposite walls together in a central region of said balloon such that the region where said walls are joined together provides a central web and the remainder of said balloon provides an expandable ring, and attaching said central web to said mount member so as to secure said expandable balloon with said mount member.

5. A method according to claim 4, wherein said opposite walls of said balloon are joined together by heat sealing.

6. A method according to claim 4 or 5, wherein said opposite walls are joined together using a die on opposite sides of said balloon, and wherein said dies are provided with cutting formations to form an aperture in said central web.

* * * * *